(12) United States Patent
Mikolajczak et al.

(10) Patent No.: US 6,602,997 B2
(45) Date of Patent: Aug. 5, 2003

(54) WHOLE CELL AND CELL-DEBRIS POLYSACCHARIDE

(75) Inventors: Marcia Mikolajczak, San Diego, CA (US); Motohide Yamazaki, San Diego, CA (US); Thomas J. Pollock, San Diego, CA (US)

(73) Assignees: Shin-Etsu Bio, Inc., San Diego, CA (US); Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/838,650

(22) Filed: Apr. 19, 2001

(65) Prior Publication Data

US 2002/0031808 A1 Mar. 14, 2002

Related U.S. Application Data

(60) Provisional application No. 60/200,082, filed on Apr. 27, 2000.

(51) Int. Cl.$^7$ .................... C08B 37/00; C12P 19/04
(52) U.S. Cl. .................. 536/123; 435/101; 435/84; 435/72
(58) Field of Search .................. 435/101, 84, 72; 536/123

(56) References Cited

U.S. PATENT DOCUMENTS 3,915,800 A * 10/1975 Kang et al. .................. 435/101
5,985,623 A    11/1999 Pollock et al.

OTHER PUBLICATIONS

Hebbar et al, Appl. Microbiol. Biotechnol. 38:248–253, 1992.*
Carbohydrate Research, Apr. 12, 2001, vol. 331, pp. 285–290, Gulin, et al. "Structural studies of S7, another exocellular polysaccharide containing 2–deoxy–arabino–hexuronic acid".
Carbohydrate Research, 1996, vol. 285, pp. 69–79, Falk, et al. "Structural studies of the exocellular polysaccharide from *Sphingomonas paucimobilis* strain 1886".

* cited by examiner

*Primary Examiner*—Francisco Prats
(74) *Attorney, Agent, or Firm*—Seed IP Law Group PLLC

(57) ABSTRACT

The present invention provides for a method for obtaining a polysaccharide substantially free from whole bacterial cells and bacterial cell debris including:

(a) fermenting a Sphingomonas bacterium, which produces the polysaccharide, to produce an aqueous fermentation broth having the polysaccharide dissolved therein;

(b) diluting the fermentation broth with an equal volume of deionized water;

(c) partially hydrolyzing the polysaccharide by exposing the fermentation broth resulting from step (b) to a temperature in excess of 100° C. for a time period from about ten minutes to about one hour;

(d) removing bacterial cells from the polysaccharide by centrifugation of the fermentation broth and recovery of a supernatant aqueous liquid;

(e) precipitating the polysaccharide from the supernatant aqueous liquid by adding a second liquid to the supernatant aqueous liquid, wherein the second liquid is miscible with water, non-reactive with the polysaccharide, and in which the polysaccharide is substantially insoluble; and (f) harvesting the polysaccharide resulting from step (e) by separating it from the supernatant aqueous liquid.

5 Claims, No Drawings

WHOLE CELL AND CELL-DEBRIS POLYSACCHARIDE

This application claims the benefit of Provisional application Ser. No. 60/200,082, filed Apr. 27, 2000.

BACKGROUND OF THE INVENTION

The present invention relates to a method of freeing a polysaccharide from a bacterial culture and the bacterial culture free polysaccharide obtained by the method. Specifically, the present invention relates to a method of freeing polysaccharide S-7 from a bacterial culture and the bacterial culture free polysaccharide S-7 obtained by the method.

Polysaccharide S-7 (hereinafter referred to as "S-7") was initially described as a polymer secreted into a culture broth by a bacterium designated as *Azotobacter indicus* var. *myxogenes* which was deposited at the American Type Culture Collection as ATCC21423. See U.S. Pat. No. 3,960,832 issued to Kang et al. on Jun. 1, 1976 which discloses a single composition of matter and U.S. Pat. No. 3,915,800 issued to Kang et al. on Oct. 28, 1975 which discloses the growth of the naturally occurring bacterial strain *Azotobacter indicus* in a submerged aerated culture in a nutrient medium and the recovery of the polysaccharide. The bacterial strain ATCC21423 was recently cultured and it was determined that the bacteria in the culture belonged to the genus Sphingomonas. See Pollock, T. J., "Gellan-related Polysaccharides and the Genus Sphingomonas," *Journal of General Microbiology*, vol. 139, pp. 1939–1945 (1993)). This culture is referred to as "Sphingomonas strain S7."

S-7 is the subject of expired U.S. Pat. No. 3,894,976 issued to Kang et al. on Jul. 15, 1975 which discloses the use of S-7 in water based paints and U.S. Pat. No. 3,979,303 issued to Kang et al. on Sep. 7, 1976 which discloses the use of S-7 in oil well drilling. In addition, U.S. Pat. No. 5,772,912 issued to Lockyer et al. on Jun. 30, 1998 discloses the use of S-7 in anti-icing formulations and U.S. Pat. No. 4,462,836 issued to Baker et al. on Jul. 31, 1984 discloses the use of S-7 in cement.

Furthermore, published literature concerning this polysaccharide includes a 1977 review by the inventors of the Kang et al. patents which is based on the information in their published patents (See Kang, K. S. and W. H. McNeely, "A New Bacterial Heteropolysaccharide, In Extracellular Microbial Polysaccharides," *American Chemical Society*, pp. 220–230 (1977)), and two brief studies by others concerning culture conditions for growing the bacterium ATCC21423 (See Lee, J. W., W. G. Yeomans, A. L. Allen, R. A. Gross, and D. L. Kaplan, "Compositional Consistency of a Heteropolysaccharide-7 Produced by *Beijerinckia indica*," *Biotechnology Letters*, 19 (1997); and Naumov, G. N., I. G. Multykh, and T. P. Shamrina, "Optimal Nitrogen and Phosphorous Concentrations in the Growth Medium for Exopolysaccharide Biosynthesis by *Beijerinckia indica*," *Mikrobiologiya*, pp. 856–857 (1985)).

All of the above mentioned patents and references disclose methods for making S-7 which is contaminated with cell debris and protein from the culture that produced the polymer. Since the S-7 polymer is secreted from the cell and remains attached to the producing cell, precipitation with any of a variety of alcohols leads to the co-precipitation of the S-7 polymer with cells, cell debris, and proteins which are present in the culture broth. After precipitation and removal of the precipitate from the solution, the aqueous solvent is transparent since all of the cells co-precipitate with the S-7 polymer. After the contaminated precipitate is recovered, dried, milled, and resuspended in liquid, the resulting viscous solution is contaminated with cells, cell debris and proteins, and has an opaque or non-transparent appearance. For certain applications, a clear viscous solution is required which lacks the particulate contaminants.

The prior art referred to above describes useful properties of the non-purified polysaccharide S-7. In particular, S-7 is soluble in hot or cold water giving a homogenous viscous mixture. The viscosity of an aqueous suspension of S-7 is highly pseudoplastic and becomes increasingly viscous at low rates of shear or at rest. The high viscosity at low shear rates makes S-7 an effective suspension agent for solids. The low viscosity at high shear rates allows the S-7 polymer solution to be transported as by pumping. The magnitude of pseudoplasticity exceeds that of xanthan gum. For shear rates between 1–10 $\sec^{-1}$, a solution of S-7 is about 3–5 times more viscous than a comparable solution of xanthan gum. The aqueous viscosity is relatively constant over a wide range of pH, temperature, and salt concentration. The viscosity is compatible with commonly encountered mono-, di- and tri-valent metal ions. However, an aqueous solution of S-7 will form a gel in the presence of di- and tri-valent metal ions if the pH is raised to 9.5–10.5, and the gel is maintained when the pH is returned to neutrality.

Polysaccharides such as S-7 have several applications, for example, as a thickener, suspending agent and stabilizer. In addition, S-7 can be used to modify the viscosity of aqueous solutions. As polysaccharides such as S-7 have several applications, it is one of the purposes of the present invention to provide polysaccharides free from contamination with cell debris and protein which could be even further effective.

SUMMARY OF THE INVENTION

Accordingly, we have discovered a novel method for obtaining a polysaccharide containing reduced amounts of contaminating cellular debris and protein. Specifically, the present invention provides for a method for obtaining a polysaccharide substantially free from whole bacterial cells and bacterial cell debris including:

(a) fermenting a Sphingomonas bacterium, which produces the polysaccharide, to produce an aqueous fermentation having the polysaccharide dissolved therein;

(b) diluting the fermentation broth obtained with an equal volume of deionized water;

(c) partially hydrolyzing the polysaccharide by exposing the diluted fermentation broth to a temperature in excess of 100° C. for a time period from about ten minutes to about one hour;

(d) removing bacterial cells from the partially hydrolyzed polysaccharide by centrifugation of the heated fermentation broth and recovering a supernatant aqueous liquid;

(e) precipitating the polysaccharide from the supernatant aqueous liquid by adding a second liquid thereto, the second liquid being miscible with water, non-reactive with the polysaccharide, and a non-solvent for the polysaccharide; and (f) harvesting the precipitated polysaccharide by separating it from the supernatant aqueous liquid.

The bacterium is preferably Sphingomonas strain S7 or a Sphingomonas bacterium modified with a S7c6 gene cluster or segment including at least the spsB and rhsACBD genes. Also, the fermentation broth preferably has a pH of about 6.

Furthermore, the method preferably includes a step of digesting contaminating cellular material by incubating the fermentation broth resulting from step (b) with at least one protease enzyme. The protease enzyme can be selected from the group consisting of Bioprase, MULTIFECT®, Protex 6L and proteinase K.

In addition, step (c) of the above method preferably includes autoclaving the diluted fermentation broth resulting from step (b) at a temperature in excess of 110° C. for about 10 to about 30 minutes. More preferably, step (c) includes autoclaving the diluted fermentation broth resulting from step (b) at a temperature of about 121° C. for about 15 minutes.

Also, it is preferable in step (d) of the above method that the bacterial cells are removed from the partially hydrolyzed polysaccharide in the fermentation broth by at least two centrifugation steps and the supernatant aqueous liquid recovered from each centrifugation step is used in the subsequent centrifugation step.

Furthermore, step (e) in the above method is preferably carried out at room temperature. In addition, the second liquid in step (e) can be selected from the group consisting of branched chain lower alkanols and lower alkyl ketones. Alternatively, the second liquid can be selected from the group consisting of methanol, ethanol, isopropanol, butanol, t-butanol, isobutanol, amyl alcohol and acetone.

Also, the polysaccharide is preferably harvested in step (f) by centrifuging the supernatant aqueous liquid to isolate a pellet of the polysaccharide. The pellet can then be pressed to remove excess of the second liquid and the pressed pellet can be resuspended in solution. Then, the polysaccharide is reprecipitated by adding second liquid to the resuspended pellet.

It is also preferable that the above method includes a step of freezing and lyophilization of the harvested polysaccharide.

The present invention also provides for a polysaccharide substantially free from whole bacterial cells and bacterial cell debris as determined by light microscopy produced by:

(a) fermenting a Sphingomonas bacterium, which produces the polysaccharide, to produce an aqueous fermentation broth having the polysaccharide dissolved therein;

(b) diluting the fermentation broth with an equal volume of deionized water;

(c) partially hydrolyzing the polysaccharide by exposing the fermentation broth resulting from step (b) to a temperature in excess of 100° C. for a time period from about ten minutes to about one hour;

(d) removing bacterial cells from the polysaccharide by centrifugation of the fermentation broth and recovery of a supernatant aqueous liquid;

(e) precipitating the polysaccharide from the supernatant aqueous liquid by adding a second liquid to the supernatant aqueous liquid, wherein the second liquid is miscible with water, non-reactive with the polysaccharide, and in which the polysaccharide is substantially insoluble; and (f) harvesting the polysaccharide resulting from step (e) by separating it from the supernatant aqueous liquid.

The bacterium is preferably Sphingomonas strain S7 or a bacterium modified with a gene S7c6 cluster or segment including at least the spsB and rhsACBD genes.

The above polysaccharide preferably includes the pyranose forms of rhamnose, glucose, and 2-deoxy-hexuronic acid arranged in the following repeating structure:

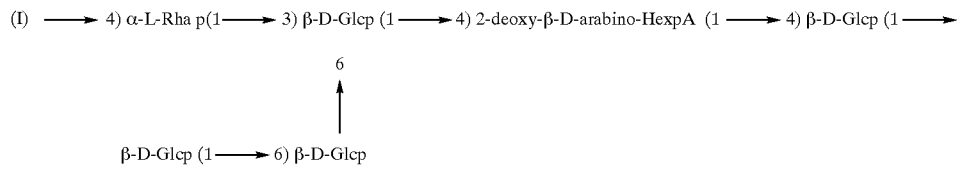

wherein Rhap is the pyranose form of rhamnose, Glcp is the pyranose form of glucose, and HexpA is the pyranose form of hexuronic acid.

Alternatively, the above polysaccharide can include the pyranose forms of rhamnose, glucose, and 2-deoxy-glucuronic acid arranged in the following repeating structure:

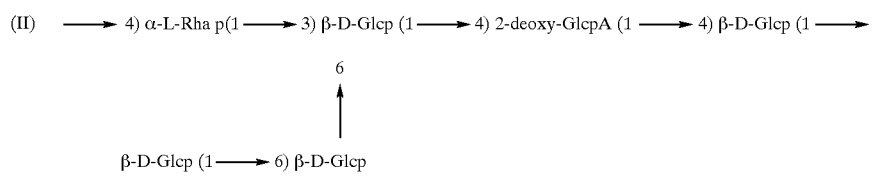

wherein Rhap is the pyranose form of rhamnose, Glcp is the pyranose form of glucose and GlcpA is the pyranose form of glucuronic acid.

The above polysaccharide in a preferred embodiment of the present invention has no side chains.

The present invention also provides for a polysaccharide substantially free from whole bacterial cells and bacterial cell debris as determined by light microscopy produced by:

(a) fermenting a Sphingomonas bacterium, which produces the polysaccharide, to produce an aqueous fermentation broth having the polysaccharide dissolved therein;

(b) diluting the fermentation broth with an equal volume of deionized water;

(c) partially hydrolyzing the polysaccharide by exposing the fermentation broth resulting from step (b) to a temperature in excess of 100° C. for a time period from about ten minutes to about one hour;

(d) removing bacterial cells from the polysaccharide by centrifugation of the fermentation broth and recovery of a supernatant aqueous liquid;

(e) precipitating the polysaccharide from the supernatant aqueous liquid by adding a second liquid to the supernatant aqueous liquid, wherein the second liquid is miscible with water, non-reactive with the polysaccharide, and in which the polysaccharide is substantially insoluble; and (f) harvesting the polysaccharide resulting from step (e) by separating it from the supernatant liquid;

wherein the bacterium is modified with a gene S7c6 cluster or segment including at least the spsB and rhsACBD genes and the polysaccharide includes the pyranose forms of rhamnose, glucose, and 2-deoxy-hexuronic acid arranged in the following repeating structure:

(III)  → 4) α-L-Rha p(1 → 3) β-D-Glcp (1 → 4) 2-deoxy-β-D-arabino-HexpA (1 → 4) β-D-Glcp (1 →
$$\phantom{xxxxxxxxxxxxxxxxxxxxxxxxxxxxxxxxxxxxxxxxx}6$$
$$\phantom{xxxxxxxxxxxxxxxxxxxxxxxxxxxxxxxxxxxxxxxxx}\uparrow$$
$$\phantom{xxxxxxxxxxxxxxxxxxxxxxxxxxxxxxxxxxxxxx}\beta\text{-D-Glcp}$$

wherein Rhap is the pyranose form of rhamnose, Glcp is the pyranose form of glucose, and HexpA is the pyranose form of hexuronic acid.

Furthermore, the present invention provides for a polysaccharide substantially free from whole bacterial cells and bacterial cell debris as determined by light microscopy produced by:

(a) fermenting a Sphingomonas bacterium, which produces the polysaccharide, to produce an aqueous fermentation broth having the polysaccharide dissolved therein;

(b) diluting the fermentation broth with an equal volume of deionized water;

(c) partially hydrolyzing the polysaccharide by exposing the fermentation broth resulting from step (b) to a temperature in excess of 100° C. for a time period from about ten minutes to about one hour;

(d) removing bacterial cells from the polysaccharide by centrifugation of the fermentation broth and recovery of a supernatant aqueous liquid;

(e) precipitating the polysaccharide from the supernatant aqueous liquid by adding a second liquid to the supernatant aqueous liquid, wherein the second liquid is miscible with water, non-reactive with the polysaccharide, and in which the polysaccharide is substantially insoluble; and (f) harvesting the polysaccharide resulting from step (e) by separating it from the supernatant liquid;

wherein the bacterium is modified with a gene S7c6 cluster or segment including at least the spsB and rhsACBD genes and the polysaccharide includes the pyranose forms of rhamnose, glucose, and 2-deoxy-glucuronic acid arranged in the following repeating structure:

wherein Rhap is the pyranose form of rhamnose, Glcp is the pyranose form of glucose and GlcpA is the pyranose form of glucuronic acid.

DETAILED DESCRIPTION OF PREFERRED EMBODIMENTS

The present invention provides for a method for obtaining a polysaccharide substantially free from whole bacterial cells and bacterial cell debris. As used herein, "substantially free" means that the polysaccharide is contaminated by not more than about 1.0% by dry weight protein. The protein concentration can be determined by standard methods well known in the art, e.g., Biorad colorimetric dye-binding assay.

The method for obtaining a polysaccharide substantially free from whole bacterial cells and bacterial cell debris includes the following steps:

(a) fermenting a Sphingomonas bacterium, which produces the polysaccharide, to produce an aqueous fermentation broth having the polysaccharide dissolved therein;

(b) diluting the fermentation broth with an equal volume of deionized water;

(c) partially hydrolyzing the polysaccharide by exposing the fermentation broth resulting from step (b) to a temperature in excess of 100° C. for a time period from about ten minutes to about one hour;

(d) removing bacterial cells from the polysaccharide by centrifugation of the fermentation broth and recovery of a supernatant aqueous liquid;

(e) precipitating the polysaccharide from the supernatant aqueous liquid by adding a second liquid to the supernatant aqueous liquid, wherein the second liquid is miscible with water, non-reactive with the polysaccharide, and in which the polysaccharide is substantially insoluble; and (f) harvesting the polysaccharide resulting from step (e) by separating it from the supernatant aqueous liquid.

The phrase "substantially insoluble" as used herein means that the second liquid is a non-solvent for the polysaccharide. The second liquid allows sufficient precipitation and recovery of the polysaccharide.

The bacterium is preferably Sphingomonas strain S7 or a bacterium modified with a gene S7c6 cluster or segment including at least the spsB and rhsACBD genes. An unmodified Sphingomonas strain S7 produces polysaccharide S-7

(IV)  → 4) α-L-Rha p(1 → 3) β-D-Glcp (1 → 4) 2-deoxy-GlcpA (1 → 4) β-D-Glcp (1 →
$$\phantom{xxxxxxxxxxxxxxxxxxxxxxxxxxxxxxxxxxxxxxxxx}6$$
$$\phantom{xxxxxxxxxxxxxxxxxxxxxxxxxxxxxxxxxxxxxxxxx}\uparrow$$
$$\phantom{xxxxxxxxxxxxxxxxxxxxxxxxxxxxxxxxxxxxxx}\beta\text{-D-Glcp}$$

which has a composition well known in the art. See the Kang et al. patents and references cited above.

A Sphingomonas strain S7 modified with a S7c6 gene cluster or segment produces an extracellular polysaccharide S7c6 (hereinafter sometimes referred to as "S7c6") which has a composition shown in a U.S. patent application _____ filed Mar. 10, 2001 and entitled "Production of Polysaccharide," which is herein incorporated by reference thereto. In particular, the extracellular polysaccharide S7c6 produced by Sphingomonas S7 containing plasmid pRK-S7c6 is composed of L-Rhap, D-Glcp, and 2-deoxy-β-D-arabino-HexpA (hereinafter referred as "2-deoxy-HexpA") in the molar ratios 1:3:1 (2-deoxy-HexpA is 2-deoxyglucuronic acid). The 2-deoxy-HexpA residue is acid-labile and was not detected by glycosyl residue and glycosyl-linkage composition analyses. Its presence was established by $^1$H and $^{13}$C NMR spectroscopy which also established the relative amounts of the glycosyl constituents. S7c6 is partially fragmented by β-elimination upon treatment with NaOH and deuterium-labeled methyl iodide ($C_2H_3I$). The fragments thus formed consist of a series of per-O-trideuteriomethylated oligosaccharides each of which is terminated at their non-reducing end with a Δ-4,5-2-deoxy-HexpA residue. Glycosyl linkage composition analysis, MALDI-TOF-MS, and one- and two dimensional-$^1$H and $^{13}$C NMR spectroscopy of these oligosaccharides established that S7c6 is composed predominantly of the following pentasaccharide repeating unit:

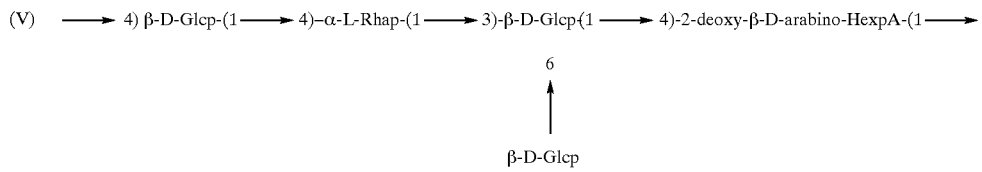

The terminal β-D-Glcp residue is absent in ~10% of the repeating units, while another ~10% of the repeating units have a second β-D-Glcp- attached to O-6 of what was the terminal β-D-Glcp residue →. Thus, the repeating unit of S7c6 can be unsubstituted or substituted with a mono- or diglucosyl side chain. The length of the side chains is the only detectable difference between S7c6 and S-7 which is the polysaccharide synthesized by the parent bacterium. Each repeating unit of S-7 has a diglucosyl side chain.

Typically, exopolysaccharides are produced by fermentation and then are usually separated from the soluble culture medium by precipitation with an organic solvent such as isopropyl alcohol. The precipitated exopolysaccharides resulting from such separation are contaminated with cells, cell debris, proteins and polyhydroxybutyrate. For example, the concentration of proteins was found to be typically between 10–15% of the dry weight of the precipitate after culturing a Sphingomonas bacterium as exemplified by U.S. Pat. Nos. 4,326,053 and 4,401,760.

In addition, an alcohol-precipitated sample was taken directly from a culture of Sphingomonas bacterium modified with a S7c6 gene or cluster, which is a derivative of Sphingomonas strain S7, without any purification treatment and was analyzed for protein content by the Biorad colorimetric dye-binding assay and it was found to contain 4–5% protein.

The method of the present invention provides for obtaining a polysaccharide containing reduced amounts of contaminating cellular debris and protein.

The following Example exemplifies a method of preparing a polysaccharide according to the present invention. The particular materials and conditions employed are intended to be further illustrative of the invention and are not limiting upon the reasonable scope thereof.

EXAMPLE

Culture Conditions and Preparation of the Polysaccharide S-7

Growth of Sphingomonas strain S7 and production of the polysaccharide S-7 has been obtained in a wide variety of liquid and solid culture media and with various conditions of agitation, aeration, temperature and pH. A useful liquid medium for submerged stirred fermentation contains 1 g $NH_4NO_3$, 3.2 g $K_2HPO_4$, 1.6 g $KH_2PO_4$, 0.2 g $MgSO_4$-$7H_2O$, 1 ml of 1000×trace minerals, 0.5 g Soy Peptone (soluble soy protein from Marcor), and 30 g D-glucose per liter of tap water. Further, 1000×trace minerals contain 270 mg $FeCl_3$-$6H_2O$, 136 mg $ZnCl_2$, 198 mg $MnCl_2$-$4H_2O$, 24 mg $CoCl_2$-$6H_2O$, 24 mg $Na_2MoO_4$-$2H_2O$, 25 mg $CuSO_4$-$5H_2O$ per 100 ml deionized water, and the solution is autoclaved before use.

In order to prepare the inoculum for bench-scale fermentation, a culture of S7 bacteria was grown in the above medium in a shaking flask at 30° C. and then aliquots of cells taken at an early stationary phase were frozen at −70° C. A frozen aliquot was thawed and about 1 ml was added to a shaking flask containing 250 ml of the above medium and incubated at 30° C. for 16 hours until early stationary phase.

About 200 ml of this seed culture was transferred into a fermentor containing 3.8 liters of the above medium. The fermentors were BioFlo models III and 3000 of New Brunswick. Agitation was from a downward-flowing three-bladed marine impeller located about 1 inch from the liquid surface and two six-bladed Rushton impellers, one located at the midpoint in the culture and one near the bottom. One volume per minute of air was supplied through a sparger below the lower impeller. The culture pH was initially adjusted to 7.0 and no further pH adjustments were made during the fermentation. The dissolved oxygen was maintained above 30% during the initial 18 hours by automatic increases in the agitation rate to a maximum of 1000 rpm, whereupon the dissolved oxygen decreased and became unmeasurable. The viscous contents of the fermentor were collected after culturing for 48 hours at 30° C. and stored in the presence of 0.01% (w/v) sodium azide at 4° C. until purification of the polymer.

A volume of 120 ml of viscous fermentation broth having a pH of about 6 was diluted with an equal volume of deionized water and then transferred into six loosely capped 50 ml polypropylene centrifuge tubes. The diluted broth was autoclaved at 121° C. for 15 minutes to partially hydrolyze the polymer and release the capsular polysaccharides from the cells, which were then removed by repeated centrifugation at about 5000–8,000×G. The polysaccharides were then precipitated from the broth at room temperature by adding 2 volumes of isopropyl alcohol. A variety of liquids can be substituted for isopropyl alcohol which is miscible in water and does not react with the polysaccharide, and in which the polysaccharide is substantially insoluble. Examples of such liquids include straight or branched chain lower alkanols such as methanol, ethanol, isopropanol, butanol, t-butanol, isobutanol, and n-amyl alcohol or lower alkyl ketones such as acetone.

The precipitate was then pressed to remove most of the isopropyl alcohol and then resuspended in 20 mM KCl and the precipitation was repeated 3 times. The final precipitate was frozen and lyophilized. A sample was tested for protein concentration using the BioRad colorimetric dye-binding assay and found to contain 0.4% as protein. A microscopic examination revealed the absence of whole cells or cell debris.

The purified sample of the polysaccharide was found to have the same HPLC profile of neutral sugars following hydrolysis with trifluoroacetic acid as is found for the non-purified polymer.

Purification of the Polysaccharide S-7 by Enzyme Treatment

The culture broth resulting from the growth of strain S7 and containing the polysaccharide was diluted with one volume of deionized water, adjusted to pH 8.0 and dispensed into 10 gram samples. The samples were then incubated at 55° C. for 30 minutes and then different types of protease enzymes including Bioprase, MULTIFECT®, Protex 6L, and proteinase K, were added to digest the contaminating cellular material. The enzyme digestions were at 55° C. for 120 minutes and then the transmittance of light at 600 nm through a 1 cm sample was measured. The transmittance through pure water was 100%. Table 1 below shows the percent (%) transmittance of light for samples including various protease enzymes.

TABLE 1

| Sample | % Transmittance |
|---|---|
| Control (no enzyme) | 24 |
| Bioprase (10 PUN) | 53 |
| Bioprase (30 PUN) | 75 |
| MULTIFECT ® (100 ppm) | 77 |
| MULTIFECT ® (300 ppm) | 83 |
| Protex 6L (100 ppm) | 84 |
| Protex 6L (300 ppm) | 87 |

The enzyme-treated broth can then be extracted as above to obtain cellular debris free polysaccharide in accordance with the invention.

The structure of the purified polysaccharide was determined by standard methods of chemical analysis, including gas chromatography and nuclear magnetic resonance spectroscopy.

Thus, while there have been described what are presently believed to be the preferred embodiments of the present invention, those skilled in the art will realize that other and further embodiments can be made without departing from the spirit and scope of the invention, and it is intended to include all such further modifications and changes as come within the true scope of the invention.

Deposits

The following two bacterial strains were deposited with the Patent Depository at the American Type Culture Collection at 10801 University Boulevard, Manassas, Va. 20110, on Jun. 29, 2000 pursuant to the Budapest Treaty for the International Recognition of the Deposit of Microrganisms:

(1) Sphingomonas strain S7 with plasmid pRK311-S7c6, also denoted as S7/pRK-S7c6; and (2) Sphingomonas strain S7 with plasmid pRK311-pgm spsB rhsACBD, also denoted as S7/pRK-pgmBrhs.

What is claimed is:

1. A polysaccharide substantially free from whole bacterial cells and bacterial cell debris produced by:

(a) fermenting a modified Sphingomonas strain S7 bacterium that produces a polysaccharide to generate an aqueous fermentation broth having the polysaccharide, wherein the bacterium is modified with either (i) an S7c6 gene cluster that is contained in plasmid pRK311-S7c6 (ATCC PTA-2174) or (ii) a segment of the S7c6 gene cluster that comprises spsB and rhsACBD genes which segment is contained in plasmid pRK311-pgm spsB rhsACBD (ATCC PTA-2175), and wherein the polysaccharide comprises the following repeating structure:

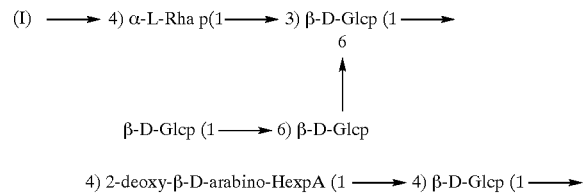

wherein Rhap is the pyranose form of rhamnose, Glcp is the pyranose form of glucose, and HexpA is the pyranose form of hexuronic acid;

(b) separating the bacteria from the polysaccharide by centrifugation of the fermentation broth and recovery of a supernatant aqueous liquid having the polysaccharide; and (c) precipitating the polysaccharide to render it separable from the supernatant.

2. A polysaccharide substantially free from whole bacterial cells and bacterial cell debris produced by:

(a) fermenting a modified Sphingomonas strain S7 bacterium that produces a polysaccharide to generate an aqueous fermentation broth having the polysaccharide, wherein the bacterium is modified with either (i) an S7c6 gene cluster that is contained in plasmid pRK311-S7c6 (ATCC PTA-2174) or (ii) a segment of the S7c6 gene cluster that comprises spsB and rhsACBD genes which segment is contained in plasmid pRK311-pgm spsB rhsACBD (ATCC PTA-2175), and wherein the polysaccharide comprises the following repeating structure:

(II) 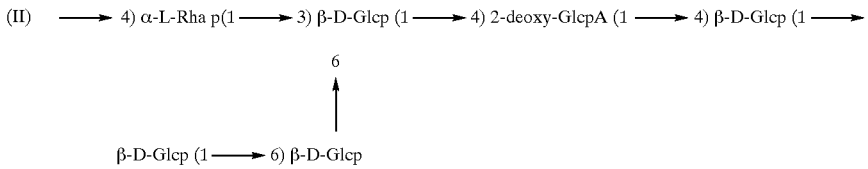

wherein Rhap is the pyranose form of rhamnose, Glcp is the pyranose form of glucose, and GlcpA is the pyranose form of glucuronic acid;
(b) separating the bacteria from the polysaccharide by centrifugation of the fermentation broth and recovery of a supernatant aqueous liquid having the polysaccharide; and
(c) precipitating the polysaccharide to render it separable from the supernatant.

3. A polysaccharide substantially free from whole bacterial cells and bacterial cell debris produced by:

(a) fermenting a modified Sphingomonas strain S7 bacterium that produces a polysaccharide to generate an aqueous fermentation broth having the polysaccharide, wherein the bacterium is modified with either (i) an S7c6 gene cluster that is contained in plasmid pRK311-S7c6 (ATCC PTA-2174) or (ii) a segment of the S7c6 gene cluster that comprises spsB and rhsACBD genes which segment is contained in plasmid pRK311-pgm spsB rhsACBD (ATCC PTA-2175), and wherein the polysaccharide comprises the following repeating structure:

(IV) 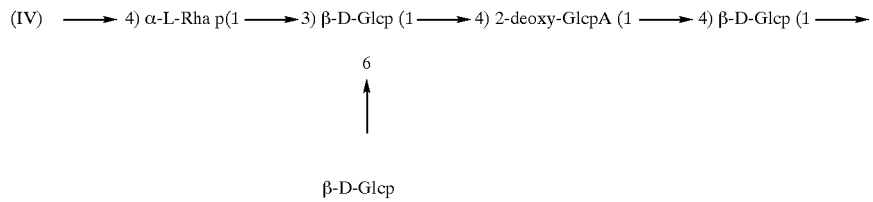

(a) fermenting a modified Sphingomonas strain S7 bacterium that produces a polysaccharide to generate an aqueous fermentation broth having the polysaccharide, wherein the bacterium is modified with either (i) an S7c6 gene cluster that is contained in plasmid pRK311-S7c6 (ATCC PTA-2174) or (ii) a segment of the S7c6 gene cluster that comprises spsB and rhsACBD genes which segment is contained in plasmid pRK311-pgm spsB rhsACBD (ATCC PTA-2175), and wherein the polysaccharide comprises the following repeating structure:

wherein Rhap is the pyranose form of rhamnose, Glcp is the pyranose form of glucose, and GlcpA is the pyranose form of glucuronic acid;
(b) separating the bacteria from the polysaccharide by centrifugation of the fermentation broth and recovery of a supernatant aqueous liquid having the polysaccharide; and
(c) precipitating the polysaccharide to render it separable from the supernatant.

5. A polysaccharide substantially free from whole bacterial cells and bacterial cell debris produced by:

(III) 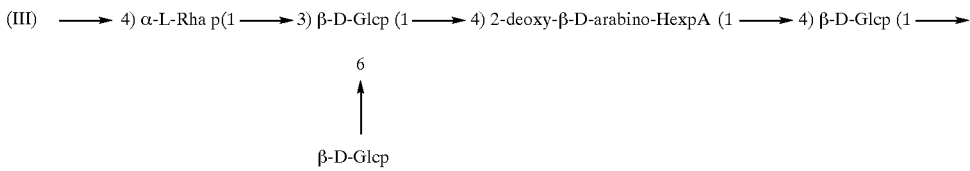

wherein Rhap is the pyranose form of rhamnose, Glcp is the pyranose form of glucose, and HexpA is the pyranose form of hexuronic acid;
(b) separating the bacteria from the polysaccharide by centrifugation of the fermentation broth and recovery of a supernatant aqueous liquid having the polysaccharide; and
(c) precipitating the polysaccharide to render it separable from the supernatant.

4. A polysaccharide substantially free from whole bacterial cells and bacterial cell debris produced by:

(a) fermenting a modified Sphingomonas strain S7 bacterium that produces a polysaccharide to generate an aqueous fermentation broth having the polysaccharide, wherein the bacterium is modified with either (i) an S7c6 gene cluster that is contained in plasmid pRK311-S7c6 (ATCC PTA-2174) or (ii) a segment of the S7c6 gene cluster that comprises spsB and rhsACBD genes which segment is contained in plasmid pRK311-pgm spsB rhsACBD (ATCC PTA-2175), and wherein the polysaccharide has no side chains;

(b) separating the bacteria from the polysaccharide by centrifugation of the fermentation broth and recovery of a supernatant aqueous liquid having the polysaccharide; and (c) precipitating the polysaccharide to render it separable from the supernatant.

* * * * *